United States Patent
Mojdehbakhsh et al.

(10) Patent No.: US 10,279,121 B2
(45) Date of Patent: *May 7, 2019

(54) DUAL CHAMBER MIXING DEVICE FOR A SYRINGE

(71) Applicant: UNL Holdings LLC, New York, NY (US)

(72) Inventors: Ramin Mojdehbakhsh, Sparta, NJ (US); Peter J. Dungar, York, PA (US); Ashley W. Palmer, Cary, NC (US); Robert E. Johannesson, Mechanicsburg, PA (US); Philip A. Weaver, Denver, PA (US); Aaron M. Weir, York Haven, PA (US)

(73) Assignee: UNL Holdings LLC, New York, NY (US)

( * ) Notice: Subject to any disclaimer, the term of this patent is extended or adjusted under 35 U.S.C. 154(b) by 561 days.

This patent is subject to a terminal disclaimer.

(21) Appl. No.: 14/920,069

(22) Filed: Oct. 22, 2015

(65) Prior Publication Data

US 2016/0038688 A1 Feb. 11, 2016

Related U.S. Application Data

(63) Continuation of application No. 13/566,079, filed on Aug. 3, 2012, now Pat. No. 9,205,194.
(Continued)

(51) Int. Cl.
*A61M 5/28* (2006.01)
*A61M 5/315* (2006.01)
(Continued)

(52) U.S. Cl.
CPC ........ *A61M 5/31596* (2013.01); *A61M 5/284* (2013.01); *A61M 5/286* (2013.01);
(Continued)

(58) Field of Classification Search
CPC .................................................. A61M 5/284
See application file for complete search history.

(56) References Cited

U.S. PATENT DOCUMENTS 2,591,706 A 4/1952 Lockhart
3,066,670 A 12/1962 Stauffer
(Continued)

FOREIGN PATENT DOCUMENTS

CN 2577863 Y 10/2003
FR 2741810 A1 6/1997
(Continued)

OTHER PUBLICATIONS

Australian Patent Office, International Search Report in International Patent Application No. PCT/AU2012/000925 (dated Oct. 5, 2012) 7 pages.
(Continued)

*Primary Examiner* — Bhisma Mehta
*Assistant Examiner* — Matthew A Engel
(74) *Attorney, Agent, or Firm* — Hamilton, Brook, Smith & Reynolds, P.C.

(57) ABSTRACT

A mixing device and a retractable syringe comprising same are provided. The mixing device comprises concentric outer and inner barrels that form an outer chamber, the inner barrel having an inner chamber. A mixing plunger is slidably located in the outer chamber. A seal located in the outer chamber is capable of axial movement, in response to depression of the mixing plunger, from a first position in sealing engagement with one or more apertures in the inner barrel to a second position intermediate the apertures and vents in the outer barrel. This allows depression of the mixing plunger to force a first substance from the outer chamber through the apertures to mix with a second substance in the inner chamber. The mixed substance in the
(Continued)

inner barrel is then delivered by the syringe with subsequent needle retraction.

14 Claims, 11 Drawing Sheets

Related U.S. Application Data

(60) Provisional application No. 61/515,554, filed on Aug. 5, 2011, provisional application No. 61/545,653, filed on Oct. 11, 2011.

(51) Int. Cl.
  *A61M 5/31* (2006.01)
  *A61M 5/32* (2006.01)
  *A61M 5/19* (2006.01)

(52) U.S. Cl.
  CPC ...... *A61M 5/3129* (2013.01); *A61M 5/31511* (2013.01); *A61M 5/3234* (2013.01); *A61M 5/19* (2013.01); *A61M 5/3202* (2013.01); *A61M 2005/3123* (2013.01); *A61M 2005/3231* (2013.01); *A61M 2005/3236* (2013.01); *A61M 2005/3238* (2013.01); *A61M 2207/00* (2013.01); *Y10T 29/49826* (2015.01)

(56) References Cited

U.S. PATENT DOCUMENTS

| | | | |
|---|---|---|---|
| 3,662,753 A | 5/1972 | Tassell | |
| 3,739,947 A | 6/1973 | Baumann et al. | |
| 3,749,084 A | 7/1973 | Cucchiara | |
| 3,872,864 A | 3/1975 | Allen, Jr. | |
| 4,188,949 A | 2/1980 | Antoshkiw | |
| 4,411,163 A | 10/1983 | White | |
| 4,643,723 A | 2/1987 | Smit | |
| 4,655,747 A | 4/1987 | Allen, Jr. | |
| 4,820,275 A | 4/1989 | Haber et al. | |
| 4,834,714 A | 5/1989 | Lascar et al. | |
| 5,078,691 A | 1/1992 | Hamacher | |
| 5,211,285 A | 5/1993 | Haber et al. | |
| 5,300,030 A | 4/1994 | Crossman et al. | |
| 5,312,336 A | 5/1994 | Haber et al. | |
| 5,395,326 A | 3/1995 | Haber et al. | |
| 5,496,284 A | 3/1996 | Waldenburg | |
| 5,593,391 A | 1/1997 | Stanners | |
| 5,643,206 A | 7/1997 | Fischer | |
| 5,807,323 A | 9/1998 | Kriesel et al. | |
| 5,851,197 A | 12/1998 | Marano et al. | |
| 6,027,482 A | 2/2000 | Imbert | |
| 6,132,400 A | 10/2000 | Waldenburg | |
| 6,248,095 B1 | 6/2001 | Giambattista et al. | |
| 6,387,078 B1 | 5/2002 | Gillespie, III | |
| 6,491,667 B1 | 12/2002 | Keane et al. | |
| 6,793,646 B1 | 9/2004 | Giambattista et al. | |
| 7,112,188 B2 | 9/2006 | Waldenburg | |
| 7,169,132 B2 | 1/2007 | Bendek et al. | |
| 7,399,295 B2 | 7/2008 | Waldenburg | |
| 7,402,150 B2 | 7/2008 | Matsumoto et al. | |
| 7,935,087 B2 | 5/2011 | Judd et al. | |
| 8,021,333 B2 | 9/2011 | Kaal et al. | |
| 8,096,971 B2 | 1/2012 | Bassarab et al. | |
| 8,945,048 B2 | 2/2015 | Thorley et al. | |
| 9,205,194 B2* | 12/2015 | Mojdehbakhsh | A61M 5/284 |
| 2002/0035348 A1 | 3/2002 | Hjertman | |
| 2002/0183690 A1 | 12/2002 | Arnisolle | |
| 2004/0097874 A1 | 5/2004 | Griffiths et al. | |
| 2004/0236273 A1 | 11/2004 | Tanaka et al. | |
| 2005/0154357 A1 | 7/2005 | Pinel | |
| 2005/0277886 A1 | 12/2005 | Hommann et al. | |
| 2006/0111666 A1 | 5/2006 | Hommann et al. | |
| 2007/0060877 A1* | 3/2007 | Bassarab | A61M 5/2448 604/89 |
| 2007/0270710 A1 | 11/2007 | Frass et al. | |
| 2010/0047914 A1 | 2/2010 | Peyman et al. | |
| 2010/0094214 A1 | 4/2010 | Abry et al. | |
| 2010/0106138 A1 | 4/2010 | Chavarria | |
| 2010/0249753 A1 | 9/2010 | Gaisser et al. | |
| 2010/0298811 A1 | 11/2010 | Connair | |
| 2012/0053516 A1 | 3/2012 | Cronenberg et al. | |
| 2013/0060231 A1 | 3/2013 | Adlon et al. | |
| 2013/0060232 A1 | 3/2013 | Adlon et al. | |

FOREIGN PATENT DOCUMENTS

| | | |
|---|---|---|
| JP | H02302265 A | 12/1990 |
| TW | 201125609 A | 8/2011 |
| WO | WO 00/62839 A2 | 10/2000 |
| WO | WO 2000-062839 A2 | 10/2000 |
| WO | WO 2002/072171 A2 | 9/2002 |
| WO | WO 2005/013830 A1 | 2/2005 |
| WO | WO 2005-072801 A1 | 8/2005 |
| WO | WO 2006/058435 A1 | 6/2006 |
| WO | WO 2006-058435 A2 | 6/2006 |
| WO | WO 2006/108243 A2 | 10/2006 |
| WO | WO 2006/119570 A1 | 11/2006 |
| WO | WO 2008/087071 A1 | 7/2008 |
| WO | WO 2009/003234 A1 | 1/2009 |
| WO | WO 2010-135732 A1 | 11/2010 |
| WO | WO 2011/060541 A1 | 5/2011 |
| WO | WO 2011/075760 A1 | 6/2011 |

OTHER PUBLICATIONS

Australian Patent Office, Written Opinion of the International Searching Authority in International Patent Application No. PCT/AU2012/000925 (dated Oct. 5, 2012) 6 pages.

* cited by examiner

DUAL CHAMBER MIXING DEVICE FOR A SYRINGE

CROSS-REFERENCE TO RELATED APPLICATIONS

This application is a continuation of U.S. application Ser. No. 13/566,079 filed Aug. 3, 2012, which claims priority to U.S. Provisional Application No. 61/515,554 filed on Aug. 5, 2011, and U.S. Provisional Application No. 61/545,653, filed on Oct. 11, 2011, each of which is included by reference herein in its entirety for all purposes.

FIELD

THIS INVENTION relates to mixing devices for syringes. More particularly, this invention relates to a mixing device for a retractable syringe which enables storage, mixing, and injection of one or more pharmaceutical substances.

BACKGROUND

It is known to provide syringes that comprise a mixing device for mixing deliverable substances prior to injection. This allows, for example, a diluent to be added to a dehydrated, lyophilized, desiccated or powdered active substance immediately prior to injection, which is particularly useful for substances that are subject to degradation or loss of activity when stored in a hydrated form.

The majority of mixing devices for syringes utilize sequential chambers, wherein the syringe has one barrel having a first proximal chamber and a second distal chamber separated by, for example, a membrane or elastomeric seal. A number of such sequential-chamber mixing syringes utilize a bypass protrusion at a section of the barrel to enable fluid in the proximal chamber to bypass the dividing membrane and mix with the fluid or powder in the distal chamber.

However, some mixing syringes utilize concentric barrel configurations. The concentric barrel mixing syringes to date, however, require complex assemblies, multiple operation steps by the user, or other particular nuances that make them difficult to manufacture, assemble, or operate. For examples, some existing concentric barrel mixing syringes require concentric inner and outer barrels that are selectively rotatable with respect to each other, and require one or more sealing rings which contain a passage means therein. The barrels must be rotated to align a hole in the inner barrel with the passage means in a sealing ring. The passage means in the sealing ring includes a radially extending opening through the sealing ring and a groove extending longitudinally of the sealing ring from the radially extending opening. This arrangement being such that the groove connects the outer barrel with the radially extending opening and the radially extending opening selectively connects the groove with the hole in the inner barrel. This enables flow of fluid from the outer barrel into the inner barrel to thereby mix the fluid with a substance in the inner barrel. Such configurations require complex components and cumbersome requirements for the user to operate the device.

Other concentric barrel designs utilize outer and inner telescopic tubular elements seated inside a barrel and coaxial with the longitudinal axis. The outer tubular element and barrel form a chamber which holds a reservoir of liquid. The outer tubular element has a fluid passageway therein that allows the liquid to flow from the chamber into the inner tubular element. The inner tubular element has an end nearby the injection port with a seal thereon that has an orifice therein. This inner tubular element receives the end of the plunger with the resilient seal thereon. Accordingly, such mixing syringe configurations require three tubular elements, with the outer and inner concentric chambers residing inside a third barrel.

There are numerous complexities associated with the use of concentric barrels for mixing syringe configurations. In addition to those described above, mixing syringes utilizing concentric barrels must also address factors such as maintenance of container sterility, interaction of components for sealing, venting requirements, and distribution of internal forces, among others. Some dual chambered syringes have concentric inner and outer barrels that form an annular space to hold a fluid and utilize one or more apertures between the inner and outer barrels to enable flow of a liquid from the annular space into the inner barrel and thereby mix the liquid with a substance in the inner barrel. The liquid is forced from the annular into the inner barrel by depression of a plunger slidably movable in the annular space. First and second sealing bands are slidably received about the inner barrel in the annular space and are mutually spaced therealong. The position of the sealing bands can dictate how sterility of the fluid path is maintained, how internal forces are distributed, and how venting occurs. For example, both of the sealing bands may be initially positioned above the aperture to form a sealed annular volume for the first liquid component. Because of this arrangement, the aperture also must act as a vent to enable any air in the annular space distal to the second sealing band, which space must be sterilized, to be expelled via the aperture upon depression of the plunger. This venting requirement may cause difficulties and require additional equipment and processing steps, such as requiring filling the inner chamber under vacuum to remove all air from the inner chamber and the distal portion of the outer barrel below the second reconstitution seal.

Generally, prior art mixing devices comprising concentric barrels are complicated in structure and often require rotation of the barrels to align one or more apertures that enable a flow of a liquid substance from one chamber into another. Further to this, various sterility, sealing and venting arrangements have been used which have serious limitations in terms of ease of manufacture and operation of the mixing device.

SUMMARY

It is therefore an object of the invention to provide a mixing device and/or a syringe comprising the mixing device that alleviates one or more of the problems associated with prior art mixing devices and/or syringes, such as those referred to above.

In one aspect, the invention provides a mixing device for a syringe, said device comprising: an outer barrel and an inner barrel in a substantially coaxial relationship, said mixing device capable of comprising a plurality of mixing substances wherein at least a first mixing substance is locatable in an outer chamber between the outer barrel and the inner barrel and at least a second mixing substance is locatable in an inner chamber in said inner barrel, the inner barrel comprising one or more fluid paths through which the first mixing substance can enter the inner chamber in the inner barrel to thereby form a mixture with the second mixing substance; one or more vents in fluid communication with said outer chamber; and at least one seal located in said outer chamber which is capable of axial movement from a first position in sealing engagement with said one or more fluid paths in the inner barrel to a second position at least partly between said one or more fluid paths and said one or more vents. Suitably, the inner barrel and the outer barrel are non-rotatable with respect to each other.

The one or more fluid paths may comprise one or more apertures, holes, bores, ports, pass-throughs or conduits. These may be of any suitable shape, configuration, arrangement and/or number. Preferably, the fluid path comprises a plurality of apertures. The apertures may be radial bores (i.e., normal to the axis of the barrel), angular bores (i.e., at an angle to axis of the barrel), helical (e.g., an angular and radial path as it traverses the thickness of the barrel wall), or any number of other configurations. The number and placement of the apertures, in locational spacing and arrangement, may also be adjusted for the desired mixing characteristics. As such, these parameters of the apertures may be configured to promote the desired mixing, dilution, and other fluid flow characteristics of the mixing syringe.

Suitably, the mixing device further comprises a mixing plunger axially moveable within the outer chamber between the outer barrel and the inner barrel to facilitate entry of the at least first mixing substance into the inner chamber in the inner barrel and to facilitate axial movement of said seal from a first position in sealing engagement with said one or more fluid paths in the inner barrel to said second position intermediate or at least partly between said one or more fluid paths and said vent. The mixing plunger may have one or more extensions, such as finger and/or thumb extensions, for ease of operation or aesthetics.

Preferably, the fluid mixing device includes a plurality of seals. Preferably, the plurality of seals comprises a proximal seal and a distal seal. In a preferred embodiment, the plurality of seals comprises: a proximal seal engagably or connectably coupled, connectable or affixed to the mixing plunger and slidably moveable in the outer chamber; and said distal seal initially in a first position in sealing engagement with said one or more fluid paths in the inner barrel and slidably moveable in the outer chamber from sealing engagement with the one or more fluid paths to a second position intermediate or at least partly between said one or more fluid paths and said vent. The movement of the mixing plunger causes movement of the proximal seal to which the plunger is engaged or connectably coupled or affixed. This movement is relayed to the first mixing substance in the outer chamber and, similarly, to the distal seal. Accordingly, axial movement of the mixing plunger indirectly (i.e., without needing direct contact) facilitates axial movement of the distal seal to said second position.

Preferably, the one or more vents are operable to facilitate exit of air from the outer chamber to atmosphere when the mixing plunger and distal seal are slidably moved in the outer chamber. The one or more vents may be integrally formed in said outer barrel or may be a vent cap mounted or affixed to said inner and/or outer barrel. In either embodiment, conduits, holes, porous membranes, collapsible components and the like may be utilized. For example, in at least one embodiment the vent cap is a plastic vent cap comprising one or more vent conduits, which plastic vent cap closes the outer chamber at the distal end of the outer barrel while permitting air to pass through the one or more vent conduits to atmosphere upon depression of the mixing plunger and movement of the distal seal.

In one embodiment, the mixing device further comprises a removable safety cap. Preferably, the removable safety cap prevents undesired movement of the distal seal prior to use (e.g., during transportation). The removable safety cap may comprise a plurality of protrusions which are insertable through respective vent conduits so as to be adjacent to, or in contact with, the distal seal.

The mixing device may further comprise a barrel extension mounted to the outer barrel, or integrally formed with the outer barrel. The barrel extension may, optionally, include finger flanges or grips, or may alternatively have optional finger flanges or grips connected thereto.

The mixing device may further comprise one or more mixing plunger locks. In one embodiment, elements of the mixing plunger and the barrel extension are engageable to form said mixing plunger lock. In one particular embodiment, the mixing plunger lock prevents removal of the mixing plunger from the outer chamber during use. In another particular embodiment, the mixing plunger lock prevents proximal, axial movement of the mixing plunger after mixing is complete.

The first and second mixing substances may comprise one or more fluids or one or more solids. The first mixing substance locatable in the outer chamber may be a fluid. The fluid may be a pharmaceutically active fluid or a pharmaceutically inactive fluid, such as a diluent. The second mixing substance locatable in the inner chamber may be a pharmaceutically active solid or a pharmaceutically active or inactive fluid.

In one embodiment, the inner chamber contains a pharmaceutically active solid and the outer chamber contains a pharmaceutically inactive diluent, such as water, whereby entry of the diluent through the one or more apertures from outer chamber into the inner chamber facilitates mixing with the pharmaceutically active solid. The interaction between the diluent and the pharmaceutically active solid enables reconstitution of the pharmaceutically active solid for subsequent delivery to a patient.

In another embodiment, the inner chamber contains a pharmaceutically active solid and the outer chamber contains a pharmaceutically active fluid, whereby entry of the fluid through the one or more apertures from the outer chamber into the inner chamber facilitates mixing with the pharmaceutically active solid in the inner chamber. The interaction between the pharmaceutically active fluid and the pharmaceutically active solid enables reconstitution of the pharmaceutically active solid for subsequent delivery to a patient.

In yet another embodiment, the inner chamber contains a first pharmaceutically active fluid and the outer chamber contains a second pharmaceutically active fluid, whereby entry of the first pharmaceutically active fluid through the one or more from the outer chamber into the inner chamber facilitates mixing with the second pharmaceutically active fluid in the inner chamber. The interaction between the first pharmaceutically active fluid and the second pharmaceutically active fluid enables mixing of the pharmaceutically active fluids for subsequent delivery to a patient.

Accordingly, the mixing device may facilitate the storage of multiple component pharmaceutical substances in the outer and inner chambers, thereby maintaining the stability and efficacy of the pharmaceutical substances during transport and over prolonged periods of storage.

In another aspect, the invention provides a syringe comprising a delivery plunger, a needle assembly, and a mixing device according to the aforementioned aspect. The syringe may be utilized for storing, transporting, mixing, and injecting one or more mixing substances to treat a patient. As will be described further below, the syringe may further contain safety features which retract the needle after use, providing desirable needle-stick prevention, and prevent re-use of the syringe.

Suitably, the delivery plunger is slidably moveable within the inner barrel of the mixing device to thereby facilitate delivery of the mixed substances or mixture to a user, patient or other recipient.

In a preferred form, the syringe is a retractable syringe that comprises a retractable needle. Preferably, the delivery plunger is capable of engaging the needle to retract the needle. Suitably, retraction of the needle is facilitated by a biasing member such as a spring, elastic or other member capable of storing and releasing energy to facilitate needle retraction. It will be appreciated that the retractable syringe may comprise any needle retraction mechanism that is operable with the mixing device disclosed herein. By way of example, the needle retraction mechanism may be as described in International Publication WO2006/119570, International Publication WO2006/108243, International Publication WO2009/003234 and International Publication WO2011/075760, although without limitation thereto.

According to one embodiment, the retractable syringe comprises: a plunger comprising a biasing member, a plunger member, a plunger outer and one or more locking members, wherein the plunger member and plunger outer co-operate to releasably maintain said biasing member in an initially energized state; and a needle assembly comprising the retractable needle, wherein the retractable needle comprises a cannula and a needle body engageable by the plunger member.

Preferably, a plunger seal is mounted to the plunger member and is capable of engaging said needle body.

Preferably, the needle assembly may further comprise a needle seal that retains the retractable needle, wherein the cannula of the retractable needle passes through the needle seal to permit delivery of the mixed substances or mixture to a user, patient, or other recipient.

In at least one embodiment, the mixing plunger further comprises a release ring. Suitably, the release ring is at a proximal end of the mixing plunger (i.e., opposite the distal end which engagably or connectably coupled, connectable or affixed to the first or proximal seal) of the mixing plunger. The release ring may be a separate component or integral with the mixing plunger. In a preferred embodiment, the release ring is a smaller diameter proximal portion of the mixing plunger. The release ring may activate needle retraction after the plunger member of the retractable syringe has engaged the needle body. Upon activation of needle retraction, the plunger member and plunger outer disengage allowing the biasing member to expand from its initially energized state. The plunger outer remains substantially in contact or connection with the release ring, while the plunger member is axially translated in the proximal direction by release of the biasing member to enable retraction of the cannula and needle body.

Suitably, the retractable syringe comprises one or more delivery plunger locking systems. In one embodiment of said locking system, the plunger outer of the delivery plunger comprises a locking member which is capable of engaging the release ring of the mixing plunger after needle retraction to thereby prevent or impede further movement of the delivery plunger relative to the release ring. In another embodiment of said locking system, the plunger outer comprises a clip which engages the plunger member after retraction of the plunger member and the needle engaged therewith.

In at least one embodiment of the present invention, the retractable syringe comprises a retraction mechanism essentially as described in WO2011/075760, with the functional modifications to the release ring of the mixing plunger described above.

In yet another aspect, the invention provides a method of assembling a mixing device including the steps of:
(i) locating an outer barrel in coaxial alignment over an inner barrel that has one or more apertures in communication with an inner chamber of the inner barrel, the coaxial alignment of the outer and inner barrels forming an outer chamber, wherein the outer chamber has one or more vents in fluid communication therewith which are located distally of the one or more apertures; and
(ii) inserting a seal into the outer chamber in releasable sealing engagement with the one or more apertures.

In one embodiment, the method further includes, prior to step (i), affixing a vent cap comprising the one or more vents to a portion of the inner barrel that is located distally of the one or more apertures. Preferably, the distal end of the outer barrel is connected to the vent cap.

Preferably, the method further includes the step of inserting a needle assembly into the inner chamber located distally of the one or more apertures.

In a further aspect, the invention provides a method of manufacturing a syringe comprising a mixing device, the method including the steps of:
(i) locating a first mixing substance in an outer chamber of the mixing device and inserting a first or proximal seal in the outer chamber of the mixing device in contact with the first mixing substance;
(ii) locating a second mixing substance in an inner chamber of the mixing device;
(iii) inserting a delivery plunger into the inner barrel, wherein the delivery plunger is proximal to one or more apertures of the inner barrel; and
(iv) mounting a mixing plunger in the outer chamber, wherein the mixing plunger contacts the first or proximal seal.

In a still further aspect, the invention provides a method of operating a syringe comprising a mixing device, said method including the steps of:
(i) operating a mixing plunger of the mixing device to thereby mix a plurality of substances;
(ii) operating a delivery plunger to deliver the substances mixed at step (i) to a recipient.

In at least one embodiment, the method of operating a syringe comprising a mixing device further includes: (iii) activating a needle retraction mechanism to retract the needle into the syringe. Preferably, the activation of the needle retraction mechanism occurs after substantially all of the substances are delivered to the recipient.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION

Figures 1A, 1B:
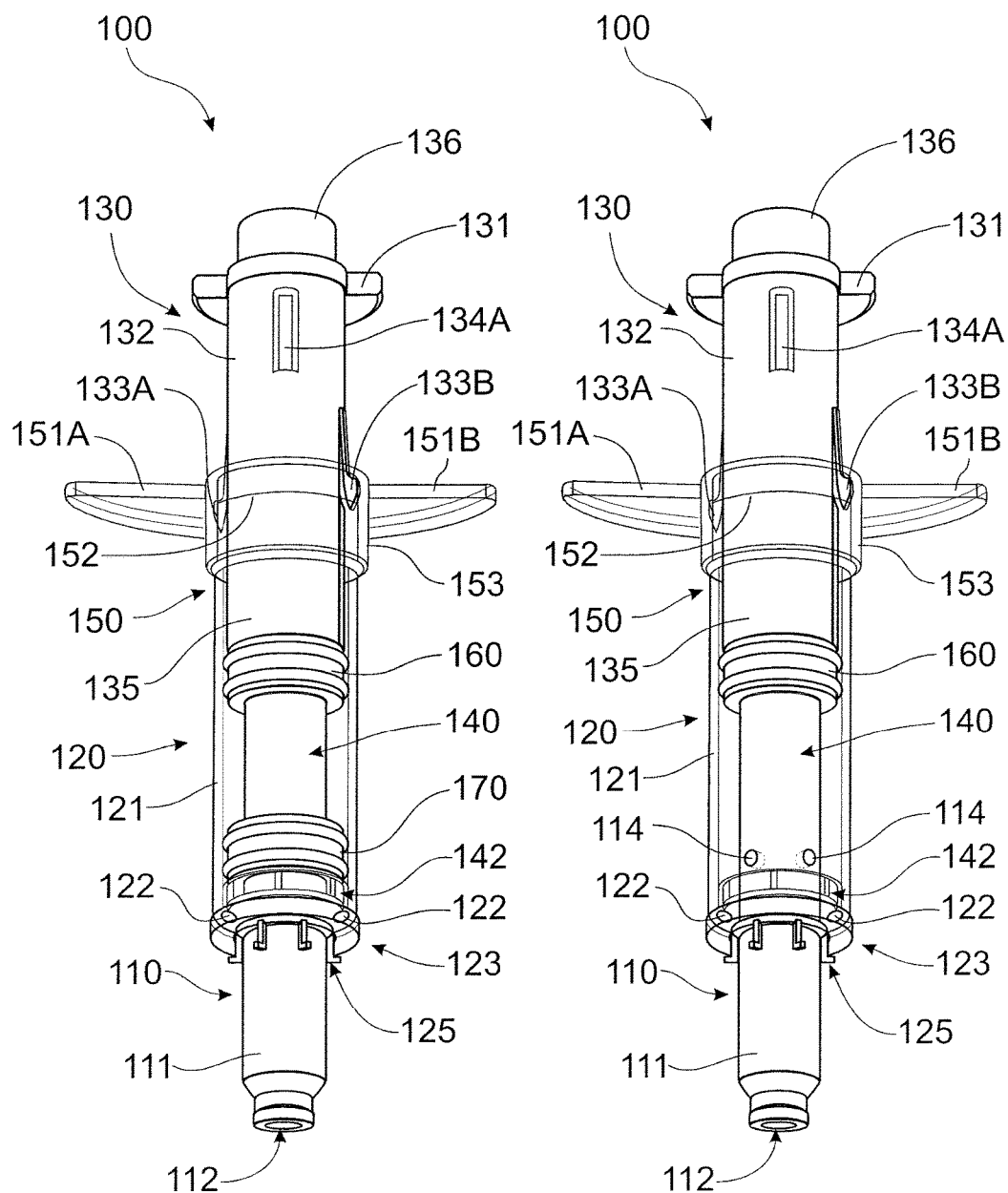
FIG. 1A shows a side view of an embodiment of a mixing device.
FIG. 1B shows a side view of an embodiment of a mixing device with distal seal removed to show fluid path apertures.

Referring to FIG. 1A and FIG. 1B an embodiment of mixing device 100 comprises inner barrel 110 comprising wall 111 and inner chamber 112, outer barrel 120 comprising wall 121 and mixing plunger 130. Outer chamber 140 is formed between wall 111 of inner barrel 110 and wall 121 of outer barrel 120. Inner barrel 110 and outer barrel 120 may be made of any of a number of materials including plastics and glass, but are preferably made of glass. Inner barrel 110 and outer barrel 120 are in a substantially concentric relationship, such that inner barrel 110 and outer barrel 120 possess a substantially common, central longitudinal axis. Inner barrel 110 and outer barrel 120 are non-rotatable with respect to each other.

Outer barrel extension 150 comprises finger grips 151A, B to assist gripping by a user. Outer barrel extension 150 may be integrally formed in outer barrel 120 or may be a separate component affixed to outer barrel 120. Outer barrel extension 150 further comprises inner lip 152 and locking ring 153, the functions of which will be described in more detail hereinafter.

Typically, outer chamber 140 contains a liquid substance and inner chamber 112 contains a solid substance, whereby the liquid substance is mixable with the solid substance in the inner chamber 112 to form a mixed substance suitable for injection. In at least one embodiment, however, the outer chamber 140 and inner chamber 112 both contact liquid substances.

In the embodiment shown in FIGS. 1A and 1B, outer barrel 120 is shorter than inner barrel 110. This configuration provides certain benefits such as, for example, allowing a heat transfer sleeve (not shown) to be placed around and in direct contact with a portion of inner barrel 110. This is useful to enable in situ lyophilization of a liquid substance located in inner chamber 112, by permitting filling with a liquid substance and then lyophilizing the liquid substance into a powder during or after manufacture of mixing device 100.

In other embodiments, inner barrel 110 and outer barrel 120 are of substantially similar length. This embodiment may be more aesthetically pleasing or provide additional volume by way of outer chamber 140. Also located in outer chamber 140 are first or proximal seal 160 and second or distal seal 170 slidably located therein. Outer barrel 120 further comprises vent cap 123 comprising plurality of vents 122, whereby vented space 142 is located between vents 122 and second or distal seal 170. Because the substances do not contact this vented space 142, vented space 142 may be unsterile and open to the atmosphere. This feature enables displacement of second or distal seal 170 towards plurality of vents 122 during the mixing step of operation, thereby opening one or more apertures 114 for passage of fluid from the outer chamber to the inner chamber. The fluid path from outer chamber 140 to inner chamber 112 remains sterile as a result of the displaced location of second or distal seal 170.

Mixing plunger 130 comprises button 131 and cylindrical shaft 132 which is slidably, axially moveable within outer chamber 140. Mixing plunger 130 may further comprise spring prongs 133A, B located on shaft 132 biased outwardly from shaft 132. Spring prongs 133A, B are moved inwardly (i.e., against bias) when inserting mixing plunger 130 into outer chamber 140 of mixing device 100. In the assembled mixing device 100, spring prongs 133A, B prevent removal of mixing plunger 130 from outer chamber 140, as will be described in more detail hereinafter. Mixing plunger 130 further comprises locking prongs 134A, B (134B not visible) located on shaft 132 biased outwardly from shaft 132. Locking prongs 134A, B are biased outwardly to engage inner lip 152 of barrel extension 150 to facilitate locking mixing plunger 130 from proximal movement after mixing is complete.

Mixing plunger 130 further comprises release ring 136 at a proximal end (i.e., proximal to a user) of cylindrical shaft 132. Release ring 136 may be a separate component or an integral component of mixing plunger 130. In a preferred embodiment, release ring 136 is a smaller diameter proximal portion of mixing plunger 130. The functions of release ring 136 will be described in more detail hereinafter.

First or proximal seal 160 is in contact with the distal end 135 of cylindrical shaft 132 of mixing plunger 130. Second or distal seal 170 is positioned distally from proximal seal 160 within outer chamber 140. First or proximal seal 160 is axially, slidably moveable within outer chamber 140 by contact with and movement of the shaft 132 of mixing plunger 130. As best seen in FIG. 1B, apertures 114 on inner barrel wall 111 provide a fluid path that allows fluid from outer chamber 140 to flow into inner chamber 112. Initially, second or distal seal 170 is in sealing engagement with apertures 114 (e.g., covering apertures 114; compare FIG. 1A and FIG. 1B).

Figure 2:
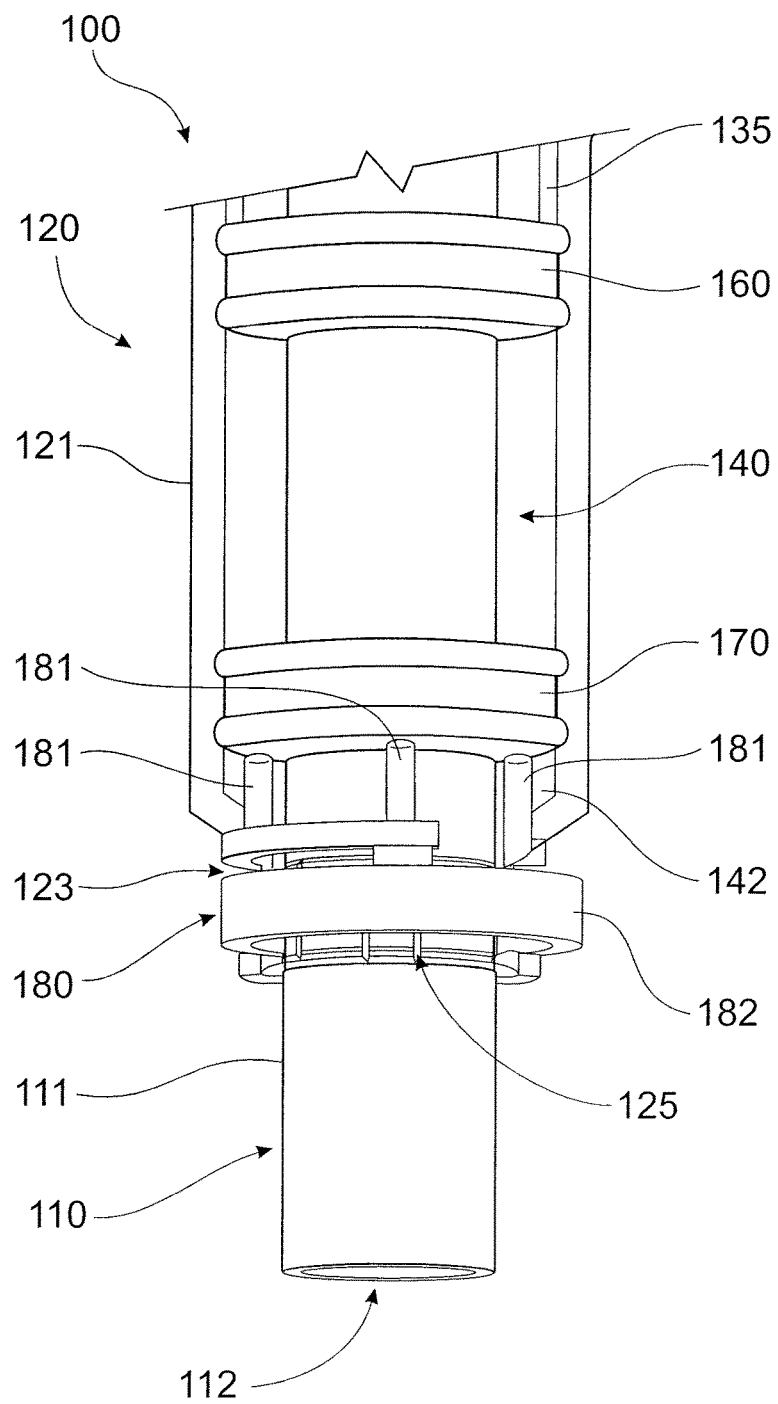
FIG. 2 shows an embodiment of a mixing device further comprising an optional safety cap mounted thereto.
Figure 3A:
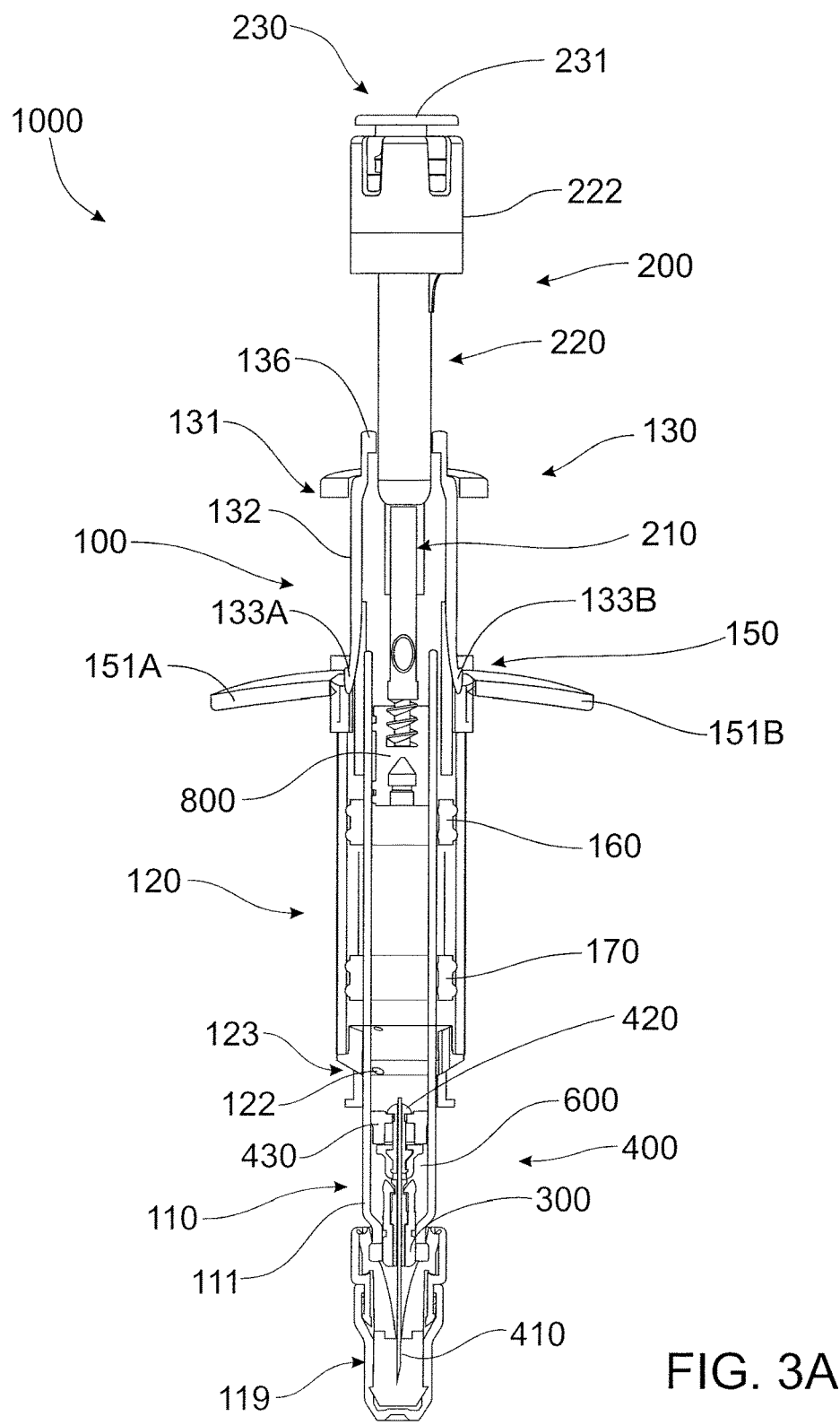
FIG. 3A shows an embodiment of a retractable syringe comprising a mixing device.
Figure 3B:
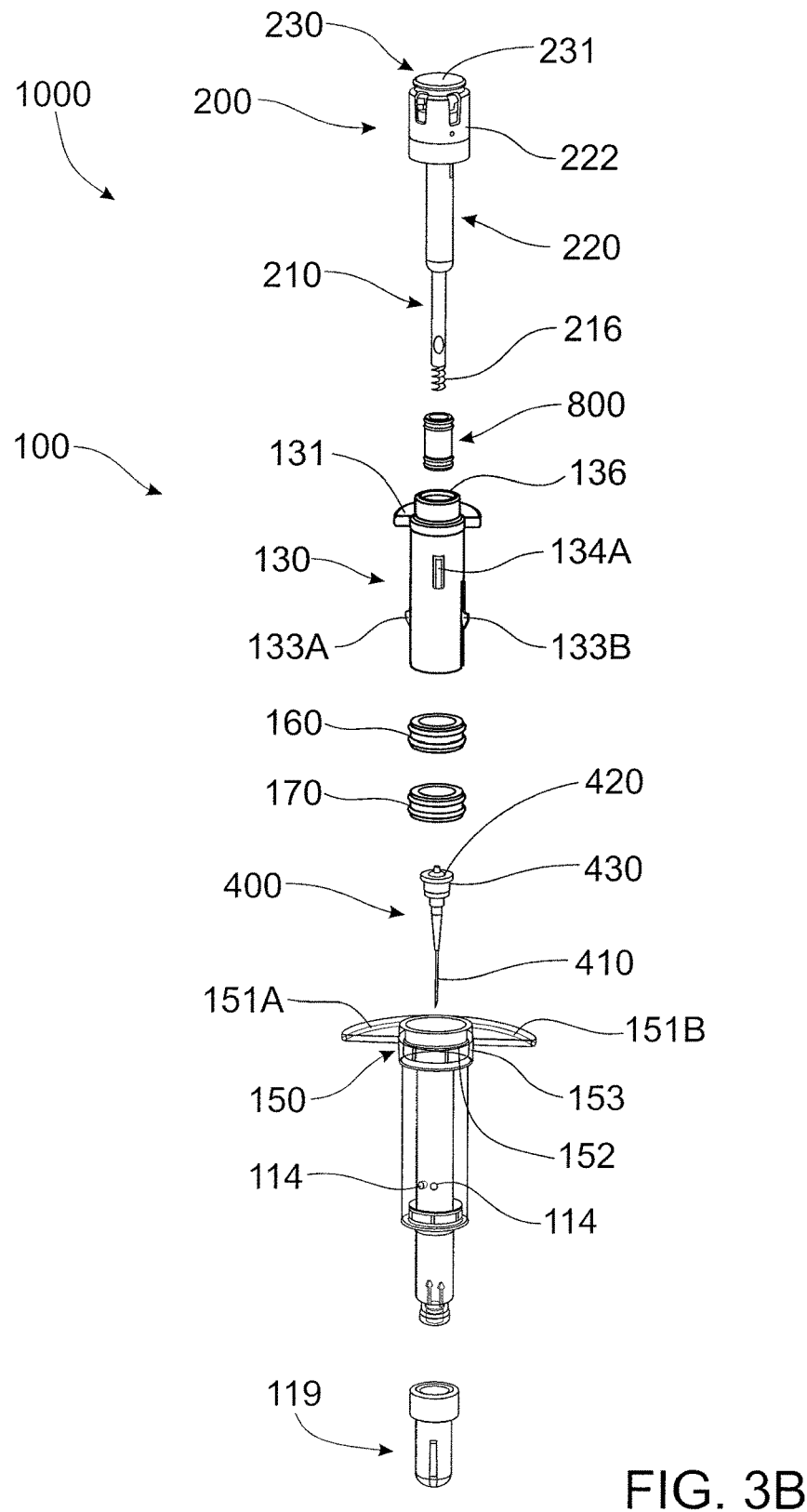
FIG. 3B shows an exploded view of an embodiment of a retractable syringe comprising a mixing device.
Figure 4:
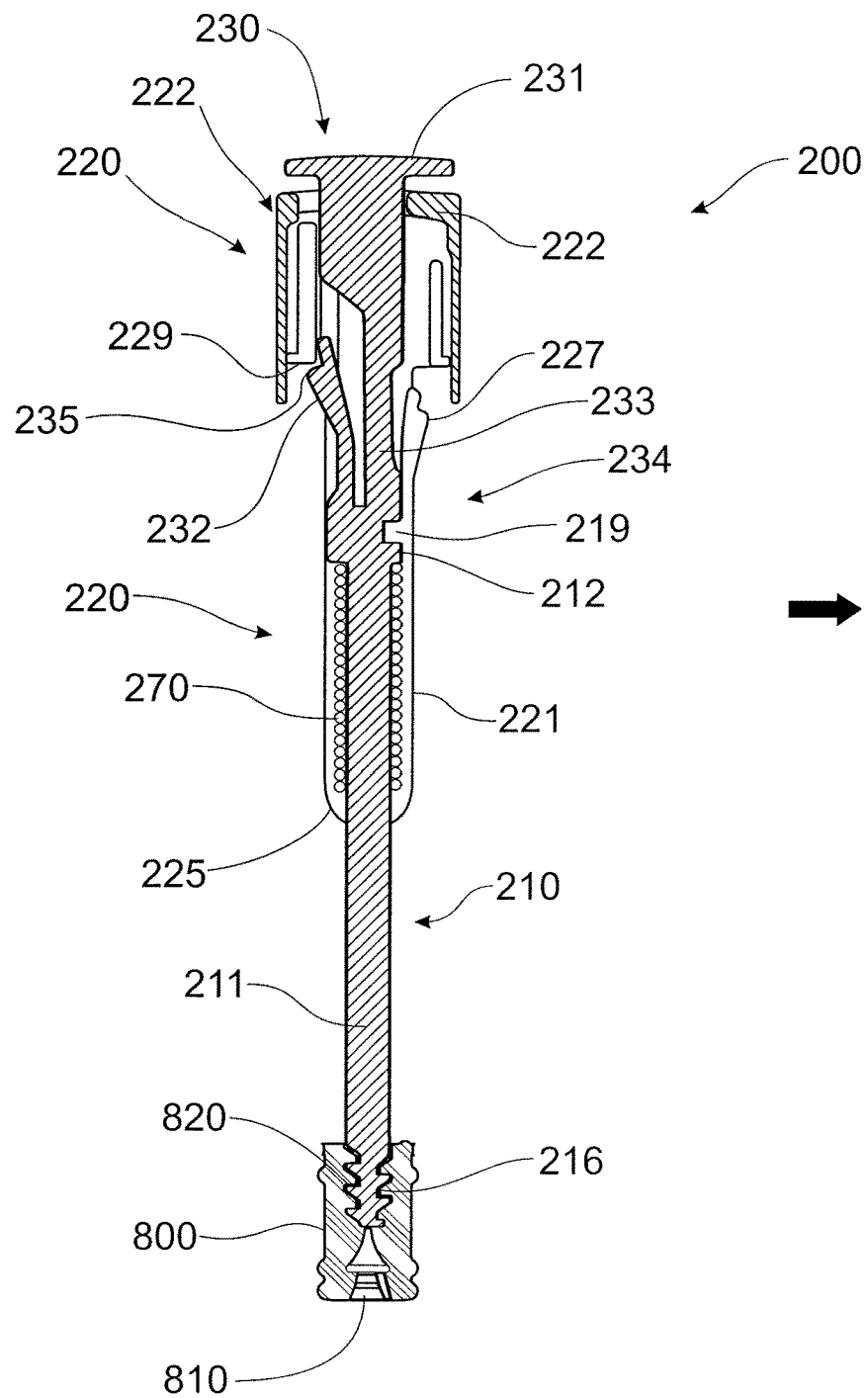
FIG. 4 shows a sectional view of a delivery plunger of a retractable syringe.
Figure 5:
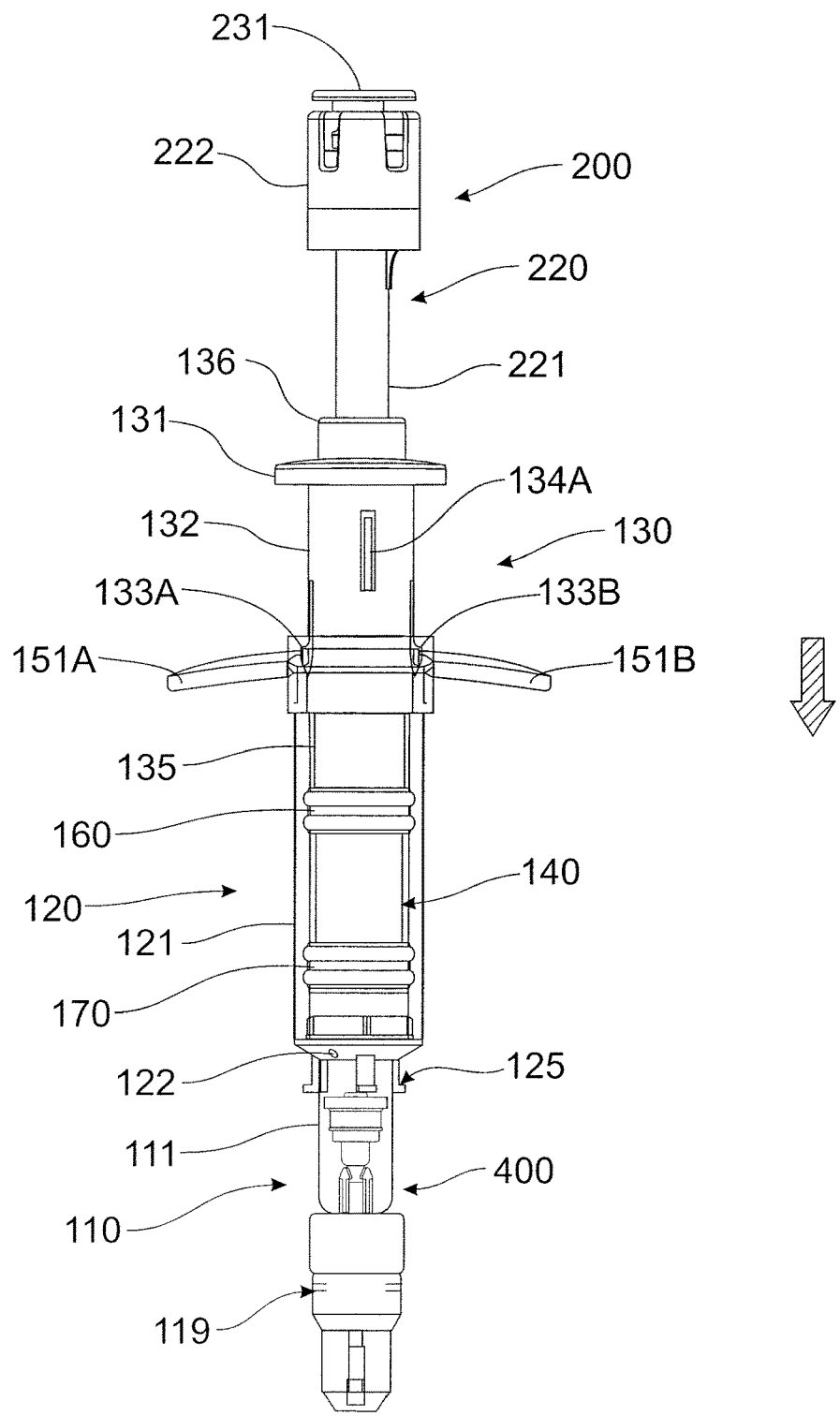
FIG. 5 shows an embodiment of a retractable syringe comprising a mixing device after removal of the safety cap prior to depression of a mixing plunger of the mixing device.

In the embodiment shown in FIG. 2, optional safety cap 180 is removably mounted to bracket 125 of outer barrel 120. Safety cap 180 comprises ring body 182 and protrusions 181 which are inserted through respective vents 122 (not visible in FIG. 2) so as to be adjacent to, or in contact with, distal seal 170. This prevents undesired movement of distal seal 170, such as in response to air pressure changes during transportation or by inadvertent movement of mixing plunger 130 prior to intended activation by the user.

Referring now to FIGS. 3-4 and FIGS. 8-10, mixing device is a component of retractable syringe 1000 that comprises delivery plunger 200 and retractable needle assembly 400. Delivery plunger 200 is axially, slidably movable in inner chamber 112 of inner barrel 110 of mixing device 100 to thereby deliver the fluid contents of the inner chamber 110 and subsequently retract retractable needle 400.

Plunger 200 comprises plunger member 210 comprising shaft 211, annular ledge 212 and seal-engaging member 216, which in this embodiment is screw threaded projection 217, which engages complementary, screw-threaded recess 820 of plunger seal 800. Plunger seal 800 further comprises needle-engaging portion 810.

Plunger 200 further comprises plunger outer 220 having elongate body 221 with base 225 and head 222 and locking member 227.

Releasably connected with plunger member 210 is control rod 230 comprising button 231, arm 232 and shaft 233. Plunger 200 further comprises compressed spring 270 which is mounted between plunger member 210 and plunger outer 220, held in an initially compressed state between ledge 212 of plunger member 210 and base 225 of plunger outer 220. In at least one embodiment, control rod 230 is releasably coupled to plunger member 210 by way of shaft 233 which is releasably connected to plunger member 210 by optional frangible junction 234 (shown in FIG. 10). Control rod 230 also releasably engages plunger outer 220 to thereby retain spring 270 in an initially compressed state held between annular ledge 212 of plunger member 210 and base 225 of plunger outer 220 in elongate portion 221. Initially, ledge 235 of arm 232 abuts rim 229 of plunger outer 220 to thereby retain control rod 230 and prevent axial movement of control rod 230 relative to plunger outer 220. However, arm 232 of control rod 230 is resiliently flexible and movable in the direction of the solid arrow shown in FIG. 4, which will allow disengagement of control rod 230 from plunger outer 220 to facilitate decompression of spring 270, as will be described hereinafter.

Needle assembly 400 comprises retractable needle 400 comprising cannula 410 and needle body 420, retainer 300, needle seal 430 and ejector 600.

Operation of mixing device 100 will be described with particular reference to FIGS. 1A, 1B, 5 and 6. In these embodiments, outer chamber 140 contains a fluid substance and inner chamber 112 contains a solid substance, whereby the fluid is mixable with the solid substance in the inner chamber 112 to form a mixed, fluid substance suitable for injection. As evident in FIG. 5, safety cap 180 (shown in FIG. 2) has been removed from outer barrel 120 to allow movement of second or distal seal in outer chamber 140.

Initially, second or distal seal 170 covers apertures 114 in inner barrel wall 111 to prevent movement of liquid from outer chamber 140 into inner chamber 112. Depression of mixing plunger 130 (i.e., axial movement towards needle 400 in the direction of the hatched arrow) in the direction of the solid arrow forces first or proximal seal 160 distally in outer chamber 140 which forces liquid contained in outer chamber 140 to displace second or distal seal 170 (i.e., towards retractable needle 400), thereby opening apertures 114 to permit fluid to transfer from outer chamber 140 to inner chamber 112.

Figure 6:
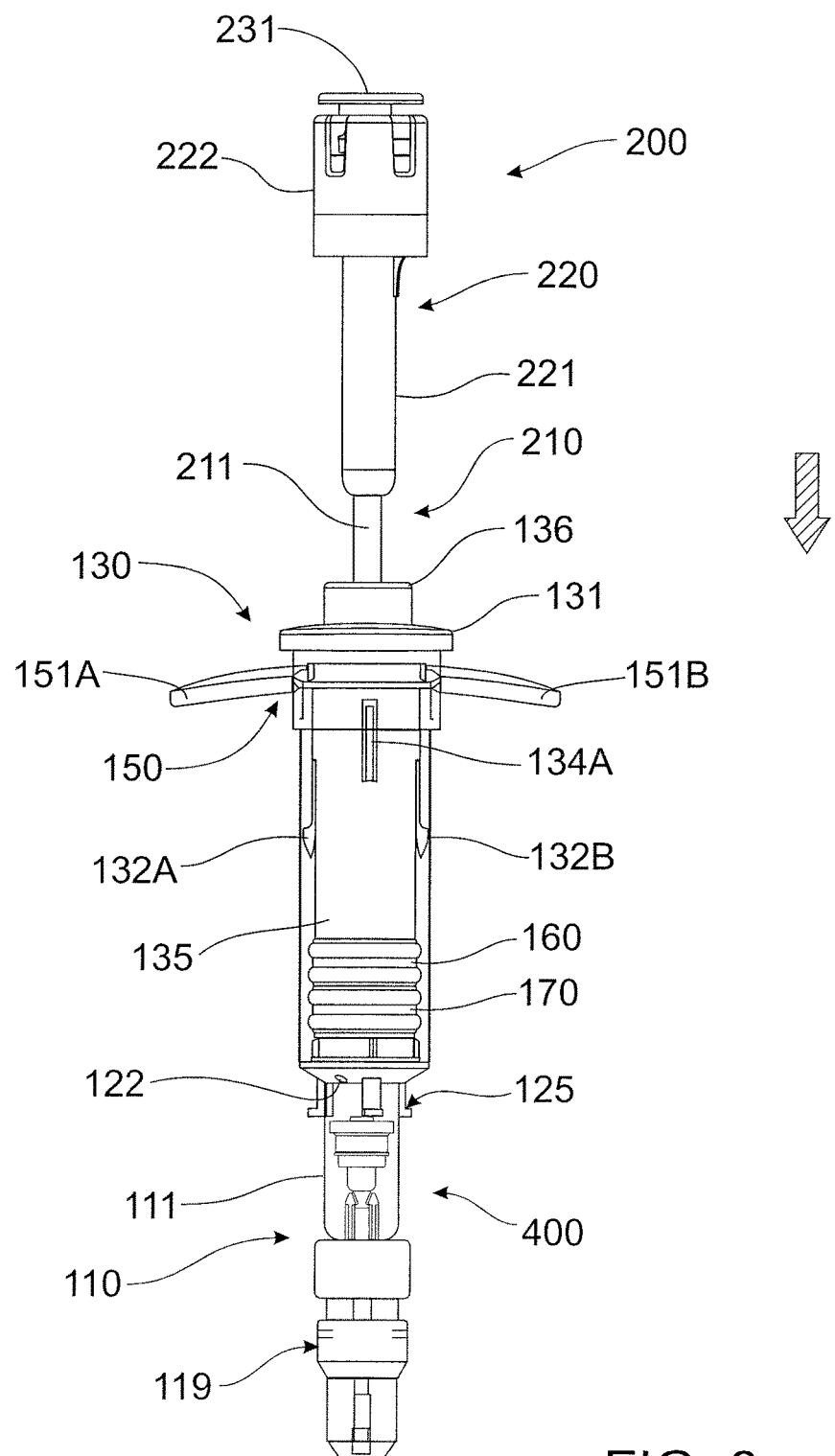
FIG. 6 shows an embodiment of a retractable syringe comprising a mixing device after depression of the mixing plunger of the mixing device.

As shown in FIG. 6, continued depression of mixing plunger 130 in the direction of the hatched arrow forces further distal movement of first or proximal seal 160 within outer chamber 140, forcing continued fluid flow from outer chamber 140 to inner chamber 112, until first or proximal seal 160 is in contact with second or distal seal 170. Seals 160 and 170 may be caused to reach end of travel within outer chamber 140, where second or distal seal 170 will contact with vent cap 123. In this position, either seal 160 is in sealing engagement (i.e., covering) with apertures 114 or both seals 160 and 170 may be in partial sealing engagement with apertures 114. The latter is possible, for example, when fluid flow from outer chamber 140 to inner chamber 112 does not require the second or distal seal 170 to fully uncover the apertures 114.

At this point, fluid delivery from outer chamber 140 to inner chamber 112 is complete. Mixing plunger 130 cannot be withdrawn from outer chamber 140, as locking prongs 134A, B on mixing plunger shaft 132 (which are outwardly biased) would engage inner lip 152 of barrel extension 150 to form a lock that prevents proximal movement (i.e., towards a user) of mixing plunger 130 beyond this point. Locking mixing plunger 130 after mixing may be useful in directing the force of delivery plunger 200 through needle 400 to inject the liquid substance, instead of forcing the liquid substance back into outer chamber 140. This may also be achieved by the final positioning of first or proximal seal 160 in sealing engagement with apertures 114. Similarly, full axial movement of mixing plunger 130 and/or engagement between mixing plunger 130 and one or more detent aspects of outer barrel 120 may unlock delivery plunger 200 or a locking aspect of inner barrel 110 to enable axial depression of delivery plunger. This provides useful user feedback to ensure that the proper injection procedures are followed with the device and that reconstitution or mixing of the drug treatment(s) is enabled prior to injection into the patient.

It will be appreciated that venting space 142 between the second or distal seal 170 and vents 122 is never in contact with any substance(s) in mixing device 100, hence there is no need to maintain sterility in the area of the venting space 142. Venting space 142 may fill with air, which is displaced out of the annular space between outer barrel 120 and inner barrel 110 and between vents 122 and the second or distal seal upon depression of mixing plunger 130 and axial movement of second or distal seal 170. Furthermore, because second or distal seal 170 initially covers apertures 114 in wall 111 of inner barrel 110, sterility of this fluid path between outer chamber 140 and inner chamber 112 is maintained during use of mixing device 100. Only second or distal seal 170 is potentially in contact with any non-sterile portion of outer barrel 120 and inner barrel 110, as fluid is caused to flow from outer chamber 140 into inner chamber 112 without ever contacting the non-sterile portion.

It will also be appreciated that retractable syringe 1000 is a "closed system," meaning there is no venting of the fluid path other than by needle injection. Accordingly, delivery plunger 200 may axially move in inner chamber 110 in the proximal direction (i.e., towards a user) in response to the distal movement of mixing plunger 130. This is because distal movement of mixing plunger 150 forces liquid from outer chamber 140 into the inner chamber 112 and increases the pressure and/or fluid volume within inner chamber 112. With rigid needle sheath 119 still closed over retractable needle 400, there is no space for volume expansion other than to force delivery plunger 200 in the proximal direction within inner barrel 120. This is a desirable response as it provides visual and tactile indication to the user that the mixing has completed and that the injection may be initiated.

Upon completion of mixing of substances in inner chamber 112, syringe 1000 is ready to use. Rigid needle shield 119 is removed, cannula 410 of needle 400 is inserted into a recipient and delivery plunger 200 is depressed to deliver the mixed, fluid contents of inner chamber 112 to the recipient. Standard medical practices, such as manual agitation of the syringe to further facilitate mixing of the substances and/or priming the syringe to remove any residual air prior to injection, may be performed prior to needle insertion and injection of fluid contents.

Figure 7:
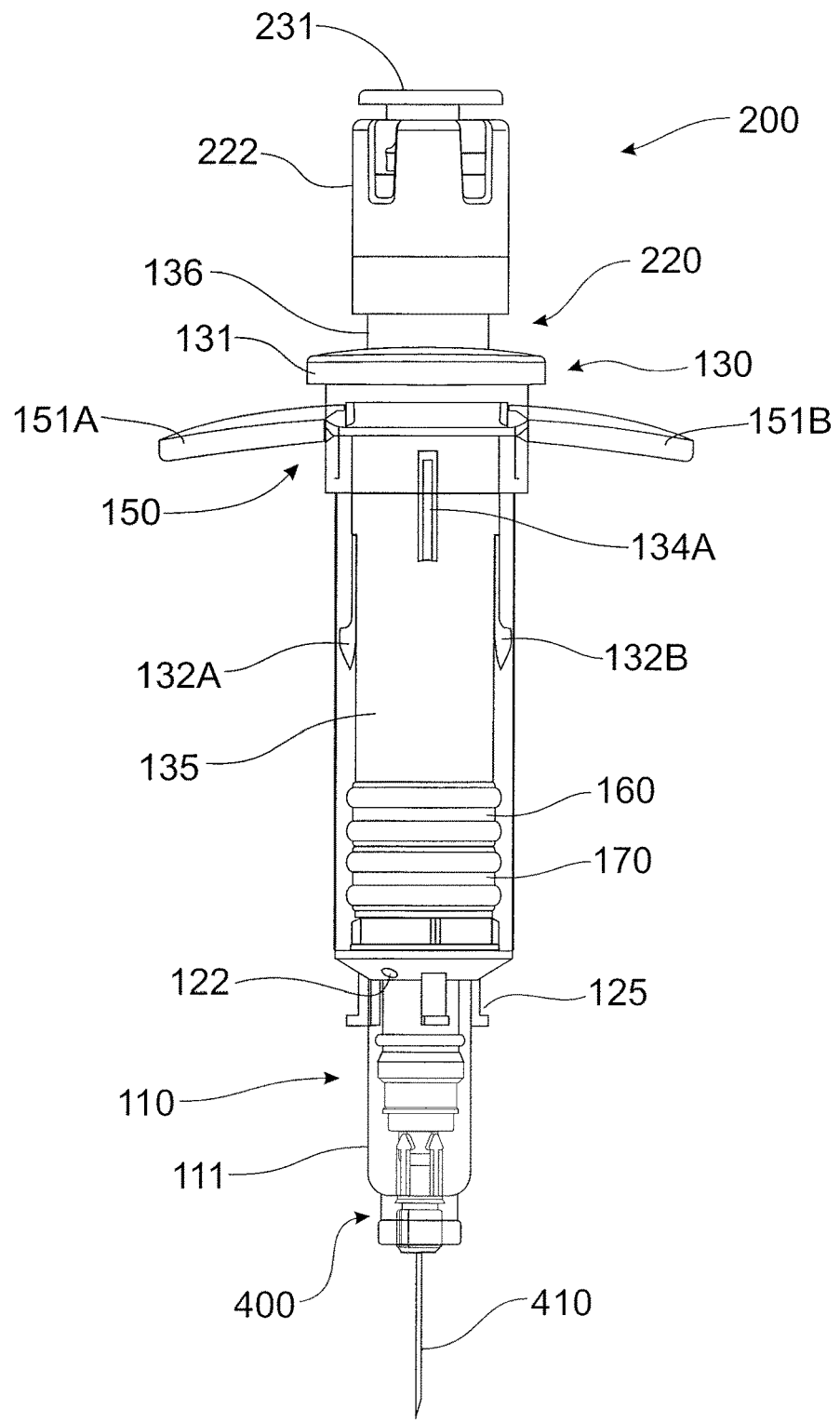
FIG. 7 shows an embodiment of a retractable syringe comprising a mixing device after depression of the delivery plunger.
Figure 8:
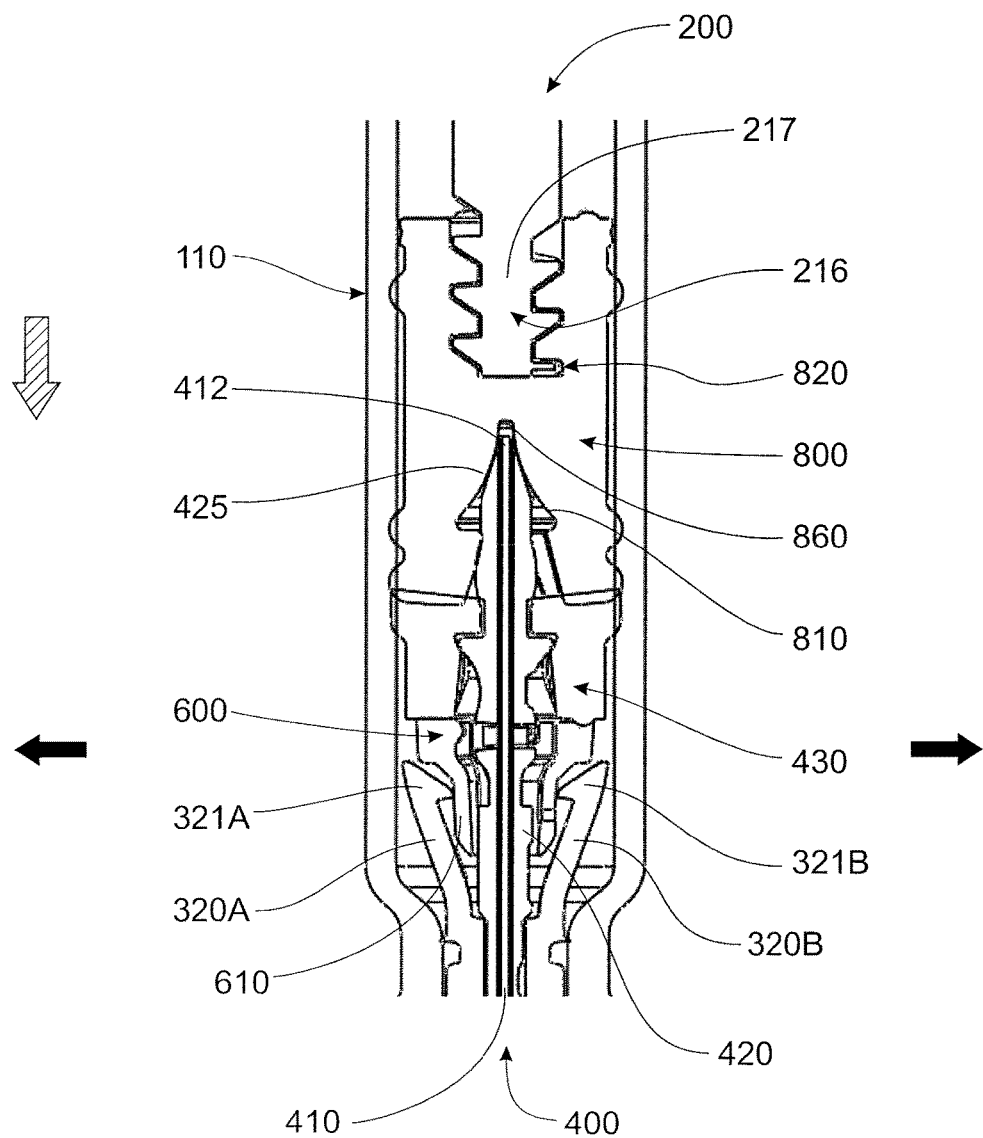
FIG. 8 shows an embodiment of a needle assembly engaged by a delivery plunger prior to retraction.

In at least one embodiment of the present invention, the needle retraction is essentially similar to that described in WO2011/075760, and will be briefly described as follows with reference to FIGS. 7-9. During delivery of fluid contents, delivery plunger 200 moves axially through barrel 110 in the direction of the solid arrow in FIG. 7. As shown in FIG. 8, plunger seal 800 bears against needle seal 430, which in turn bears against ejector 600. Further to this, ejector ring 610 moves hook-ends 321A, B of arms 320A, B of retainer 300 radially outwardly in the direction of the solid arrows in FIG. 8, thereby disengaging needle body 420 from retainer 300 to release retractable needle 400 for subsequent retraction. At this point, recessed seat 810 of plunger seal 800 has engaged segment 425 of retractable needle body 420 and recess 860 has received fluid end 412 of cannula 410. This effectively couples retractable needle 400 to plunger member 210.

Figure 9:
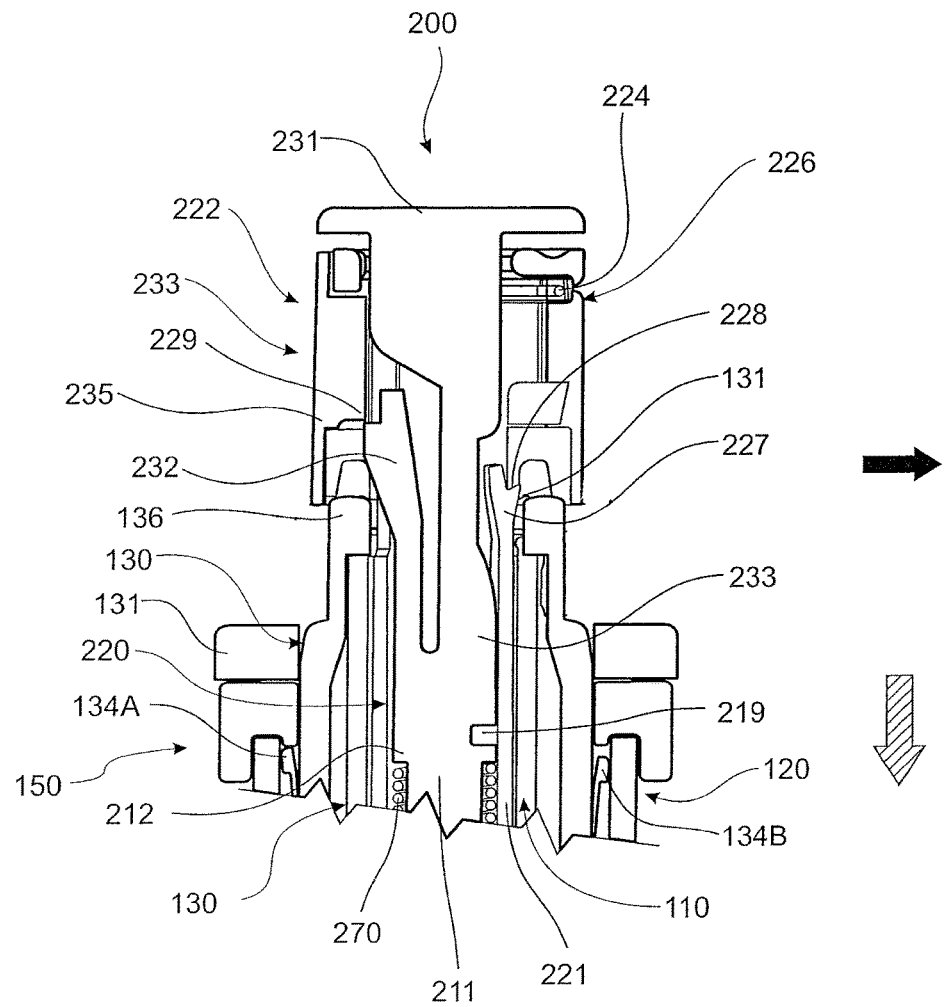
FIG. 9 shows an embodiment of a release ring disengaging a plunger outer from a plunger inner to facilitate spring decompression and needle retraction.

As shown in FIG. 9, in order for retractable needle 400 to retract at the end of delivery of fluid contents, compressed spring 270 must decompress, which is facilitated by plunger member 210 disengaging from plunger outer 220. This disengagement is facilitated by release ring 136. As plunger member 210 and plunger outer 220 are substantially fully depressed (i.e., axially translated in the distal direction as per the hatched arrow) to inject fluid from inner chamber 110, one or both may contact release ring 136. Through this contact, release ring 136 moves arm 232 radially inwardly (in the direction of the solid arrow) and out of engagement with rim 229 of plunger outer 220. This disengagement allows compressed spring 270 to decompress and push against ledge 212 of plunger member 210 to thereby retract plunger member 210 with control rod 230 coupled thereto. Plunger outer 220 remains substantially in contact or connection with release ring 136, while plunger member 210 coupled to needle body 420 and cannula 410 is axially translated in the proximal direction by decompression of spring 270, thereby retracting cannula 410 and needle body 420.

Figure 10:
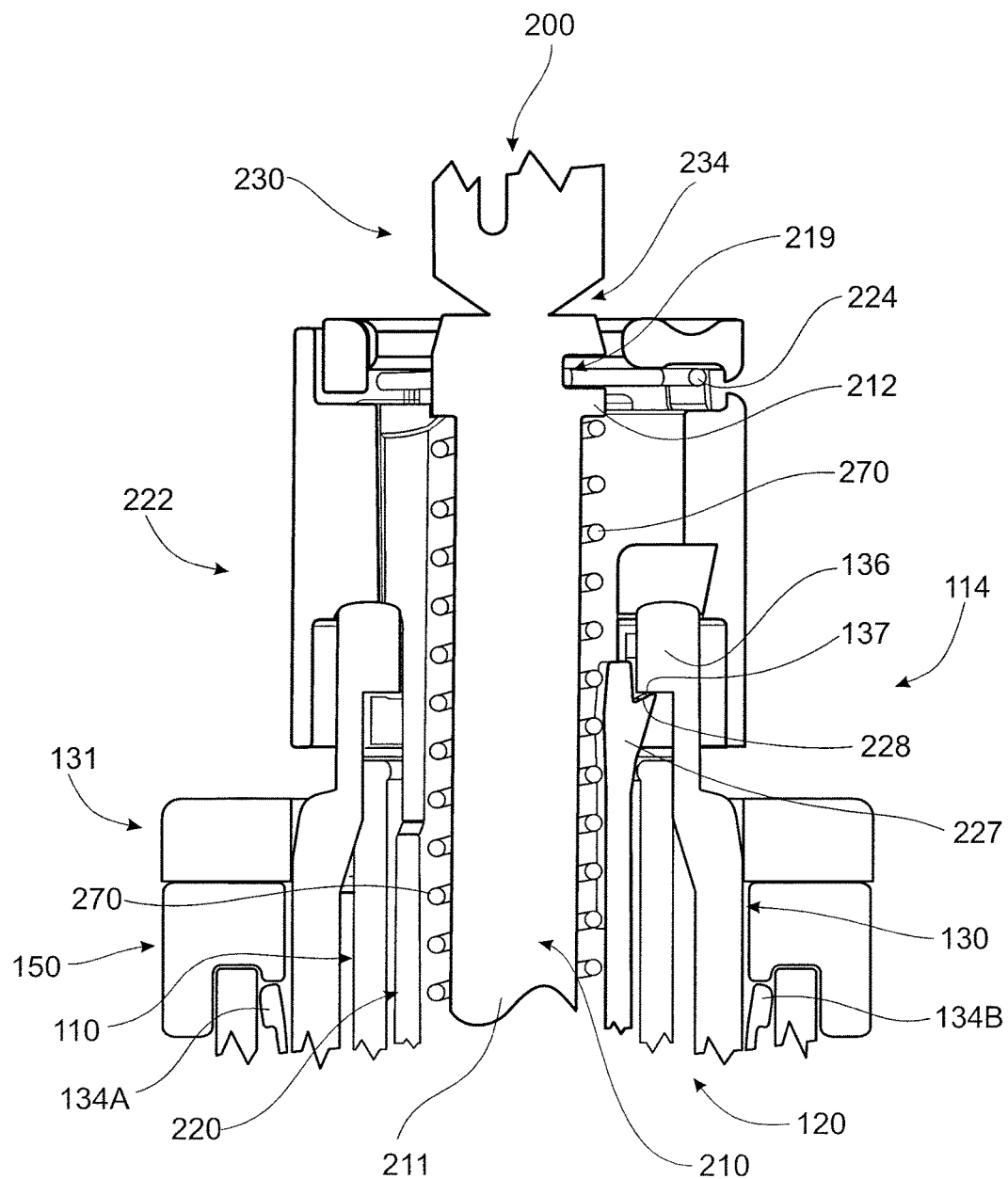
FIG. 10 shows an embodiment of locking systems of a retractable syringe.

Suitably, retractable syringe 1000 comprises one or more locking systems for delivery plunger 200. As shown in FIG. 10, in one embodiment of said locking system, plunger outer 220 of delivery plunger 200 comprises locking member 227 which comprises edge 228 engaging underside 137 of release ring 136 after needle retraction to thereby prevent or impede further movement of delivery plunger 200 relative to the release ring, as shown in FIG. 10. Accordingly, in addition to initially assisting in the activation of needle retraction, the release ring 136 may secondarily function to lock delivery plunger 200 after initial use to thereby prevent re-use.

Another of said one or more locking systems for plunger 200 is also shown in FIG. 10. After retraction, clip 224 of plunger outer 220 and locking groove 219 of plunger member 210 co-operate to form a locking system that locks plunger member 210 and plunger outer 220 together and prevent movement of plunger member 210 relative to plunger outer 220.

At the end of refraction of plunger member 210 and retractable needle 410, control rod 230 can optionally be broken from plunger member 210 at optional frangible junction 234 and manually removed from retractable syringe 100 and discarded as "clean" waste so that there is little if any plunger member 210 protruding externally from the syringe with which to attempt to force delivery plunger 200 back into barrel 110 and attempt to re-engage the needle (not shown). This optional frangible junction 234 (shown in FIG. 10) may be located along plunger member 210 at a point that would extend in the proximal direction beyond head 222 when the syringe is in the retracted position and, optionally, locked from re-use.

Certain other variations of mixing device 100 are contemplated. As an alternative to rigid needle sheath 119, a venting rigid needle shield may include a first protective component and a second protective component, the first and second components being slidably engaged such that venting may occur when the components are slid apart to an expanded state. When the first and second components are in an engaged and contracted state, no venting is permitted through the needle end. However, when the first and second components are in an engaged but expanded state (e.g., slid apart along an axis), air is permitted to vent through the needle without risk of exposing the needle to the patient. Such venting through the needle may be used, if needed, to vent the change in air volume and/or pressure within inner chamber 112 upon displacement of fluid from outer chamber 140 into inner chamber 112.

In another variation, at the end of depression mixing plunger 130 may be locked to outer barrel 120 by way of complementary detent aspects (not shown) which engage at a point of axial travel in the distal direction by mixing plunger 130 to prevent subsequent axial travel in the proximal direction. These complementary detents may be used together with, or as an alternative to, locking prongs 134A, 134B described previously.

In yet another variation, barrel extension 150 may include the aforementioned complementary detent aspects (not shown) of outer barrel 120 which engage mixing plunger 130 upon full axial translation of mixing plunger in the distal direction.

In yet another variation, inner chamber 140 may be compartmentalized (i.e., comprising a plurality of compartments) such as by one more frangible or porous membranes, walls, sealing members or the like, with each compartment containing a different fluid or solid substance, whereby depression of mixing plunger 130 facilitates mixing of each different fluid or solid substance. Additionally, or alternatively, inner chamber 112 may be similarly compartmentalized, each compartment comprising a different fluid or solid substance. Accordingly, mixing device 100 may include two or more substances for mixing and injection.

It will be appreciated from the foregoing that the mixing device and syringe disclosed herein provide an efficient and easily-operated system for mixing multiple substances prior to delivery by the syringe. There is no need to rotate or otherwise orient the inner and outer barrels prior to use to open or align fluid pathways, unlike in many prior art mixing devices such as those previously described. The positioning of the distal seal relative to the vents in the outer barrel and the apertures in the inner barrel keeps the contents of the mixing device sterile while providing adequate venting, which is in contrast to many prior art mixing devices such as previously described.

Assembly and/or manufacturing of mixing device 100, retractable syringe 1000, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization fluids and processes may be employed during the manufacture of the novel components and devices. To add the one or more apertures to the inner barrel, known drilling or boring methodologies such as mechanical or laser drilling may be employed. Furthermore, known sterilization processes may be employed at one or more of the manufacturing or assembly stages to ensure the sterility of the final product.

In one embodiment, a method of assembling the mixing device includes the steps of:

(i) affixing a vent cap having one or more vents to a distal end of an inner barrel, wherein the inner barrel has one or more apertures passing therethrough and the vent cap is affixed distally of the one or more apertures;

(ii) placing an outer barrel in coaxial alignment over an inner barrel and connecting the distal end of the outer barrel to the vent cap, wherein the outer barrel has a diameter greater than the diameter of the inner barrel and the barrels are aligned such that the annular space between the barrels forms an outer chamber;

(iii) inserting a distal seal into the outer chamber and positioning the distal seal in sealing engagement with the one or more apertures; and (iv) inserting a needle assembly into the inner chamber, such that the needle assembly resides distally of the apertures.

As discussed above, a glue or adhesive may be utilized to affix one or more components of the mixing device to each other. Alternatively, one or more components of the mixing device may be a unified component. For example, the venting cap may be a separate component affixed by a glue to the inner and outer barrels, or the venting cap may be a preformed aspect at the distal end of the outer barrel which is glued to the inner barrel. These components may be sterilized individually or together, and may be assembled in a sterile environment or sterilized after assembly. One or more of the barrels may be siliconized prior to or after assembly.

The mixing device may be utilized as a component of a mixing syringe. In one embodiment, the method of manufacturing a syringe comprising a mixing device includes the steps of:

(i) at least partly filling a first fluid substance in the outer chamber and inserting a proximal seal into the outer chamber in contact with the first fluid substance;

(ii) at least partly filling a second fluid substance in the inner chamber and inserting a delivery plunger into the inner barrel, wherein the delivery plunger is proximal to the apertures of the inner barrel; and (iii) mounting a mixing plunger in the outer chamber, wherein the mixing plunger may rest in contact with the proximal seal.

A number of known filling processes and equipment may be utilized to achieve the filling steps of the syringe manufacturing process. In one embodiment, the second fluid substance may be filled as a liquid substance and lyophilized in situ using certain barrel heat transfer equipment. The needle assembly, delivery plunger, and other components described in these manufacturing and assembly processes may be as described above or may be a number of similar components which achieve the same functionality as these components.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

What is claimed is:

1. A mixing device for a syringe, said mixing device comprising:
    an inner barrel including an inner chamber,
    an outer barrel disposed about at least a portion of the inner barrel, the outer barrel including an outer chamber at least partially formed between the inner barrel and the outer barrel,
    a distal seal disposed within the outer chamber, the distal seal separating the outer chamber into a first mixing substance space disposed proximally to the distal seal and a vented space disposed distally to the distal seal,
    the outer barrel including at least one vent extending through the outer barrel to fluidly connect the vented space with an exterior of the mixing device, the at least one vent being disposed distally to the distal seal,
    at least one aperture extending through the inner barrel and opening into the inner and outer chambers,
    the distal seal being slidably disposed within the outer chamber for movement in a distal direction between a first and a second position, the second position being distal to the first position, wherein movement of the distal seal from the first position to the second position expels air from the vented space in the outer barrel through the at least one vent as a volume of the vented space is reduced.

2. The mixing device of claim 1 wherein movement of the distal seal from the first position to the second position results in a reduction in the volume of the vented space.

3. The mixing device of claim 1 wherein the distal seal covers the at least one aperture when the distal seal is disposed in the first position, and the distal seal at least partially uncovers the at least one aperture to fluidly connect the inner chamber and the first mixing substance space when the distal seal is in the second position.

4. The mixing device of claim 1 further including a proximal seal disposed within the outer chamber proximally to the distal seal, the proximal seal being adapted for sliding movement in the distal direction within the outer chamber, the proximal and distal seals along with the inner and outer barrels defining the first mixing substance space, the distal seal and the outer and inner barrels defining the vented space distal to the distal seal.

5. The mixing device of claim 4 wherein movement of the proximal seal in the distal direction results in movement of the distal seal from the first position to the second position and the expulsion of air from the vented space to the exterior of the mixing device.

6. The mixing device of claim 1 further including a mixing plunger axially movable within the outer barrel, movement of the mixing plunger in the distal direction resulting in movement of the distal seal in the distal direction.

7. The mixing device of claim 6 wherein the mixing plunger includes a proximal seal disposed within the outer chamber proximally to the distal seal, the proximal seal being adapted for sliding movement in the distal direction within the outer chamber, the proximal and distal seals along with the inner and outer barrels defining the first mixing substance space, the distal seal and the outer and inner barrels defining the vented space distal to the distal seal, depression of the mixing plunger moving the proximal seal in the distal direction, movement of the proximal seal in the distal direction resulting in movement of the distal seal in the distal direction.

8. The syringe comprising a delivery plunger, a needle and the mixing device according to claim 7, the delivery plunger being axially, slidably movable in the inner chamber.

9. The syringe of claim 8 further including a biasing member capable of storing and releasing energy to facilitate retraction of the needle into the syringe.

10. The syringe of claim 9,
wherein the delivery plunger includes the biasing member, a plunger member, a plunger outer and one or more locking members; wherein the biasing member is a spring; wherein the plunger member and plunger outer cooperate to releasably maintain said biasing member in an initially energized state; the syringe further comprising a needle assembly comprising the retractable needle, wherein the retractable needle comprises a cannula and a needle body engageable by the plunger member.

11. The mixing device of claim 6, further comprising a mixing plunger lock which prevents removal of the mixing plunger from the outer chamber of the mixing device.

12. The mixing device of claim 1 wherein the outer barrel includes a vent cap disposed at a distal end of the outer chamber, the at least one vent extending through the vent cap.

13. The mixing device of claim 12 wherein the outer barrel further includes a cylindrical wall, the vent cap being disposed at a distal end of the cylindrical wall.

14. The mixing device of claim 1 further including a removable safety cap having at least one protrusion corresponding to the at least one vent, the at least one protrusion being disposed within a respective at least one vent and adjacent to or in contact with a distal surface of the distal seal to inhibit axial movement of the distal seal, the at least one protrusion being removable from the at least one vent to fluidly connect the vented space with a exterior of the outer barrel.

* * * * *